United States Patent

Kaule et al.

[11] 4,105,333
[45] Aug. 8, 1978

[54] METHOD OF IDENTIFYING FLUORESCENT MATERIALS

[75] Inventors: Wittich Kaule; Gerhard Stenzel, both of Munich, Fed. Rep. of Germany

[73] Assignee: G.A.O. Gesellschaft fur Automation und Organisation mbH, Fed. Rep. of Germany

[21] Appl. No.: 729,021

[22] Filed: Oct. 4, 1976

[30] Foreign Application Priority Data

Oct. 17, 1975 [AT] Austria .................................. 7944/75

[51] Int. Cl.$^2$ ............................................ G01N 21/52
[52] U.S. Cl. ...................................... 356/85; 250/365; 250/459; 250/461 R; 356/71
[58] Field of Search ...................... 356/51, 71, 188, 85; 250/271, 365, 458, 459, 461 R

[56] References Cited

U.S. PATENT DOCUMENTS

| | | | |
|---|---|---|---|
| 2,951,164 | 8/1960 | Timms | 250/461 R |
| 3,473,027 | 10/1969 | Freeman et al. | 250/365 |
| 3,492,478 | 1/1970 | Smith | 250/271 |
| 3,663,813 | 5/1972 | Shaw | 250/461 R |

*Primary Examiner*—F. L. Evans
*Attorney, Agent, or Firm*—McGlew and Tuttle

[57] ABSTRACT

In the method, light from an ultraviolet light source is directed alternately through a neutral filter, uniformly damping the radiation of the light source, and through a partially absorbing filter damping only the wavelengths necessary to excite the fluorescence of a selected flourescent material, the partially absorbing light filter including the selected fluorescent material. The light passing through the filters is then directed through a first blocking filter onto a sample to be checked for the presence of a selected fluorescent material. Only the radiation from the sample is directed through a second blocking filter onto a photodetector or the like. The respective intensities of radiation of the sample, effected by the neutral filter and by the partially absorbent filter, are measured and converted into output signals indicative of the presence or absence of the selected fluorescent material. The two filters may be moved alternately into the path of the exciting beam from the light source, and the neutral filter may be either a wide band absorbing grey filter or a free opening for passage of the exciting beam from the light source. By using plural of such partially absorbing light filters, each dampling only the wavelengths necessary to excite the fluorescence of a respective fluorescent material, it is possible to distinguish between several fluorescent materials which may be present in the sample.

17 Claims, 7 Drawing Figures

METHOD OF IDENTIFYING FLUORESCENT MATERIALS

It is known from U.S. Pat. No. 3,473,027 to use differently fluorescing, visible or invisible printing inks for machine-sensible, coded data recording. To this end, the inks are provided with lanthanide ions in such a way that one will exhibit red, another orange, a third green, and a fourth blue fluorescence. After excitation of the fluorescences by means of a uniform excitation spectrum, in the checking apparatus, the fluorescent emissions are directed, by means of a prism, to photoelectric cells associated with the individual inks. Thus, the information stored by the different combinations or by the presence or absence of the individual inks is read.

This checking system has the disadvantage that only narrow bands within predetermined regions of the fluorescence spectrum are checked for the presence or absence of fluorescences without it being possible to establish the identity of the inks itself. The checking apparatus can be deceived at any time by using counterfeit inks whose fluorescent emissions do not fall within the ranges of response of the photoelectric cells. Since there is presently no better way of identifying fluorescent materials or distinguishing between fluorescences by simple means, the very coarse checking methods make it relatively easy to forge such coded information.

The object of the invention is, therefore, to provide a simple checking method which permits unambiguous identification of fluorescent materials so that genuine fluorescent materials can be distinguished from other materials.

SUMMARY OF THE INVENTION

The invention is characterized in that the fluorescent material to be checked is excited into fluorescence with light of differently damped spectral radiant intensity, and that the different radiant intensities emitted by the fluorescent material to be checked are used for identification.

The invention takes advantage of the fact that fluorescent materials absorb the exciting light at those points of their spectra where they are excitable.

In an improvement of the invention, the fluorescent material is irradiated by a light source having a very wide spectrum whose light, in a first checking process, is evenly damped throughout the width of the spectrum by inserting a grey optical filter and, in a second checking process, is so influenced with a special filter that only the wavelengths needed to excite the genuine fluorescent material are highly damped. The emission spectra resulting from these two checking processes are detected in predetermined wavelength ranges and evaluated with a logic for verification.

To damp exactly only the exciting wavelengths of the genuine fluorescent material in the second check, use is made of an optical absorption filter which contains an addition of the material to be identified or chemical components of this material.

The invention has a number of essential advantages over the prior art. For example, despite a simple set-up, the proposed checking method permits an unambiguous identification of fluorescent materials and, hence, a distinction between very similar fluorescent materials. The use of the special filter according to the invention even allows more complex excitation spectra to be checked without additional expense. Since the special filter is given its defined filtering action by adding the material to be checked, the production of the filter presents no problems despite the stringent requirements placed on the filtering action.

For an understanding of the principles of the invention, reference is made to the following description of a typical embodiment thereof as illustrated in the accompanying drawings.

DESCRIPTION OF THE PREFERRED EMBODIMENT

Europium chelate is an organometallic luminescent material exhibiting a characteristic red fluorescence and having a characteristic excitation spectrum. Since these two features allow such a material to be very well distinguished from other luminescent materials, it was proposed in U.S. Pat. No. 3,473,027, together with other fluorescent materials, for use in automatically verifiable printing inks for securities.

While there is generally no technical interest in europium chelate, which is practically unobtainable on the market, europium-containing anorganic luminescent materials are produced and processed in large quantities, especially for the manufacture of color television picture tubes. Obtaining such luminescent materials presents no difficulties because they are commercially available.

It is relatively easy to distinguish europium-containing luminescent materials from luminescent materials without europium because of the characteristic narrow-band europium emission, whereas great difficulties have been encountered in distinguishing different europium-containing fluorescent materials from one another. In view of the danger that securities marked with europium chelate are forged with the aid of luminescent materials for color television tubes, it is highly desirable, however, also to be able to distinguish between different europium-containing luminescent materials. By the checking method according to the invention, this can be accomplished quite unambiguously and without major expense using the absorption filter according to the invention.

Figure 1:
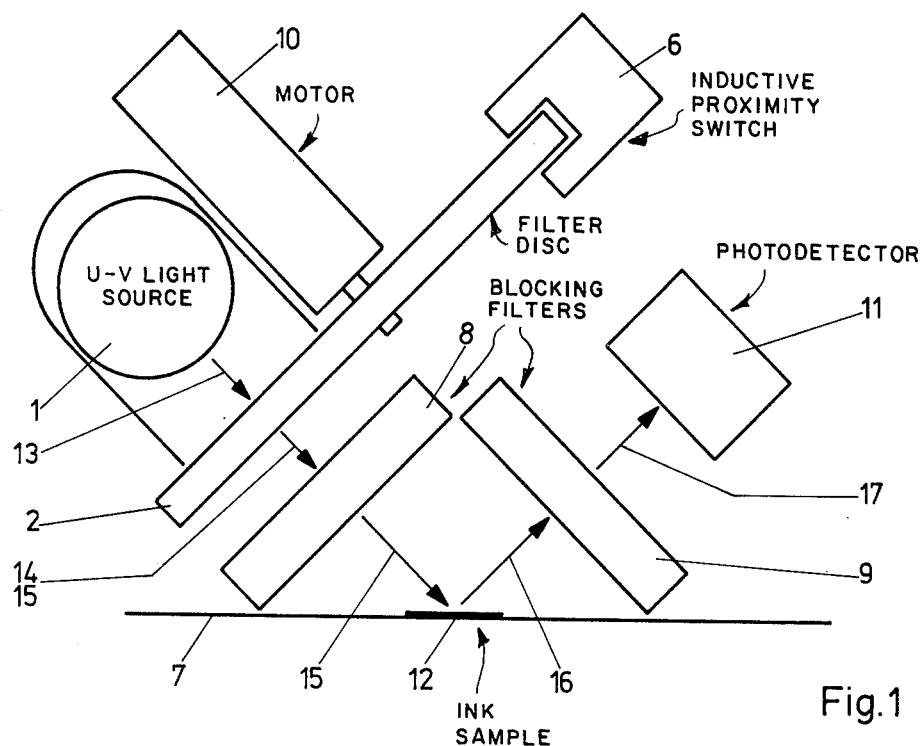
FIG. 1 is a schematic set-up of a checking apparatus operating on the principle in accordance with the invention.

FIG. 1 shows the schematic set-up of such a checking apparatus suitable for the unambiguous identification of fluorescent materials. With this apparatus, the fluorescent inks 12 deposited on the record carrier 7 are to be identified. The checking apparatus consists essentially of an exciting source 1 which radiates in the ultraviolet region with a continuous spectrum, of a rotating filter disc 2 which is driven by a motor 10 and in which two europium-chelate filters 3 and two grey filters 4, described in greater detail below, are installed in an alternate sequence, of two blocking-filter sets 8, 9, and of a photodetector 11 with which the radiant intensity emitted by the sample to be examined is measured.

Figure 2:
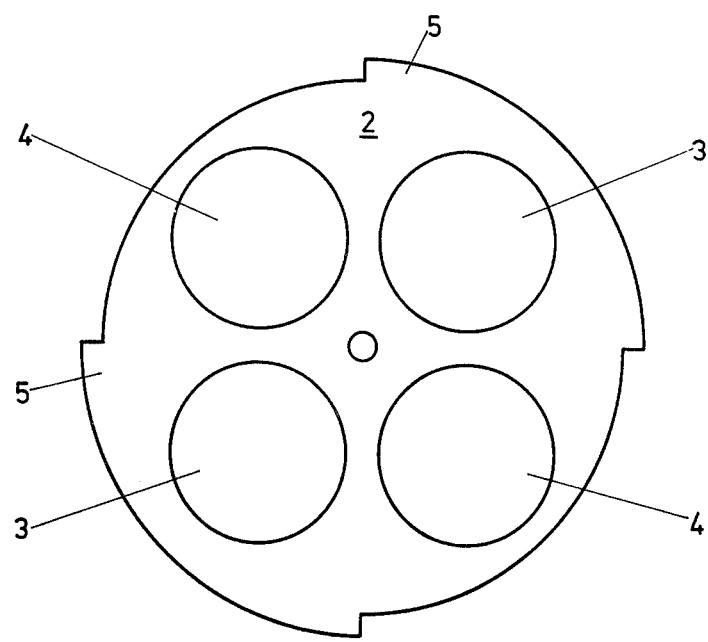
FIG. 2 is a plan view of a filter disc used in the checking apparatus of FIG. 1.

As can be seen in FIG. 2, the two europium-chelate filters 3 and the grey filters 4 are so arranged on the filter disc 2 that, when the disc is centrally driven by the motor 10, a europium-chelate filter 3 and a grey filter 4 will move between the exciting source 1 and the blocking-filter set 8 by turns. With the aid of marking portions 5 provided at the rim of the filter disc 2, and with an inductive proximity switch 6 or a similar position indicator, it can be determined at any time which of the filters 3, 4 is located in the exciting-beam path of the light source 1.

When a fluorescent material is being checked, the wide-band light spectrum of the ultraviolet light source 1 used for excitation of fluorescence passes through the filters 3, 4 of the filter disc 2 and through the blocking filter 8 to the ink sample 12 where it causes a radiation to be emitted whose intensity depends on whether a "genuine" or a "false" material is being checked and whether the grey filter 3 or the special filter 4, which is adapted to the genuine material, is located in the exciting-beam path.

The light emitted by the ink sample 12 as a result of the excitation of fluorescence passes through the blocking filter set 9 and reaches a photodetector arrangement 11 which, for a spectral resolution of the fluorescent light like in U.S. Pat. No. 3,473,027, may contain a prism and an arrangement comprising several photodetectors for detecting the europium-emission line. Since this arrangement for resolving the spectrum of the fluorescent light forms no part of the invention, it will be omitted in the following, and only a photodetector sensitive to the europium-emission line will be used behind the blocking-filter set 9. A device suitable for providing this indication is a silicon photovoltaic cell, for example.

Of the absorption filters 3, 4 shown in FIG. 2, the europium-chelate filter 3 shows an absorption behaviour by which the wavelengths needed to excite a genuine ink are highly damped, while all other wavelengths are passed undamped, as far as possible. Such a filter can be obtained, for example, by colouring acrylic glass with europium chelate. The absorption spectrum of this filter then corresponds exactly to the excitation spectrum of europium chelate. A main excitation band of europium chelate at about 350 nm is largely absorbed by this filter. As a result, considerably less radiant energy is present for the excitation of a genuine sample than, say, for that of a luminescent material for a color television picture tube, because the main excitation band of such a material, located at about 300 nm, passes the filter nearly undamped.

Figure 3:
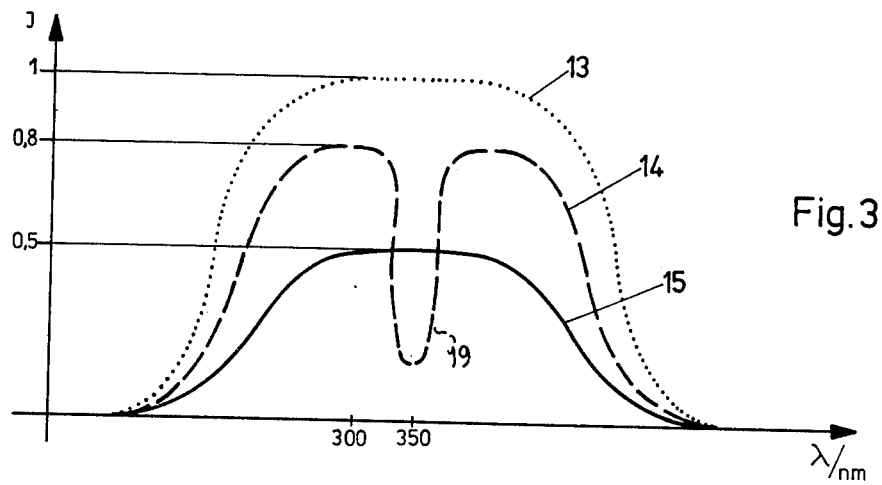
FIG. 3 is a schematic representation of the light spectra present in the checking apparatus and usable for excitation.

To obtain a reference value for the damping behaviour of the europium chelate filter 3, the grey filter 4 shows uniform damping throughout the range of radiation 13 (FIG. 3) of the exciting source 1. The transmission is chosen to be about 50%, as shown by curve 15, so that the filter 3 will damp the main excitation band of the genuine material more than will the grey filter 4, while damping the remaining spectral range less than the filter 4. The curve 14 of FIG. 3 shows this light spectrum damped by the europium chelate filter 3 and used for excitation. The partially high damping in exactly those wavelength ranges where the fluorescence of the europium chelate is excited is indicated by the fall-off 19.

Figure 4:
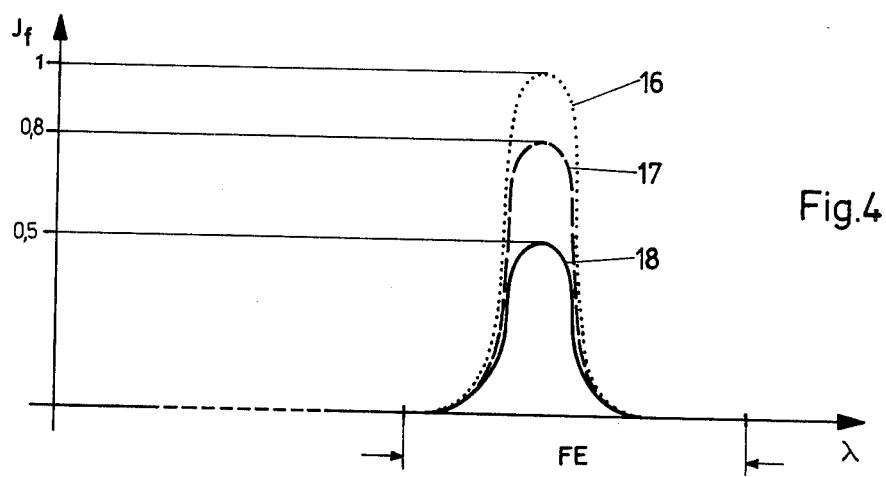
FIG. 4 is a schematic representation of the emission spectra in the checking apparatus when a false fluorescent material is being checked.
Figure 5:
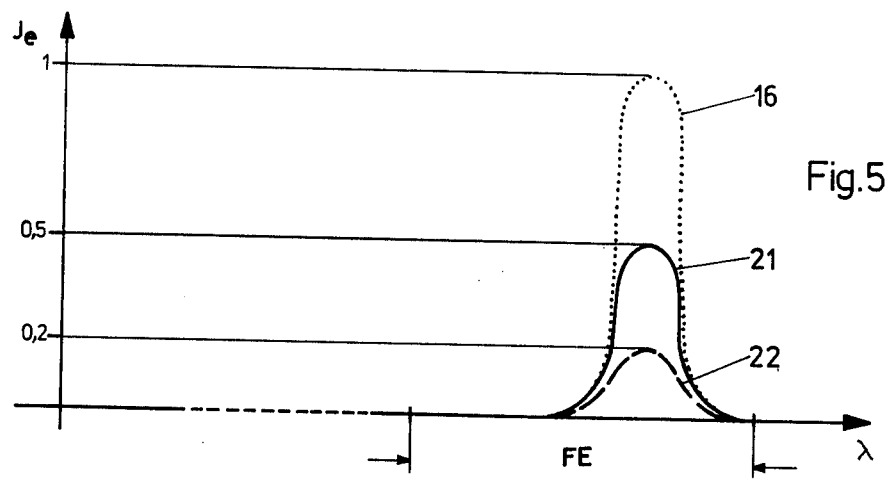
FIG. 5 is a schematic representation of the emission spectra in the checking apparatus when a genuine or selected fluorescent material is being checked.

If the above-mentioned europium inks are irradiated with the light spectra 14, 15 used for excitation, the emission spectra 17, 18, 21, 22, shown in FIGS. 4 and 5, will be obtained. The range within which the photocell responds is designated FE.

The fluorescence curves shown in FIG. 4 are obtained if a luminescent material for a television screen is irradiated, while the curves of FIG. 5 result from the excitation of the europium chelate. In reality, these spectral curves are much more complex. For the sake of simplicity, however, the invention will be explained with the aid of these highly stylized curves.

Since the damping of the filter 3 within the main excitation band of the luminescent material for a television screen (300 nm, FIG. 3) is relatively low at 0.2, the "false" ink irradiated through the filter 3 fluoresces relatively intensely ($I_f$) and, as shown by the curve 17, reaches about 80% of the value attainable with undamped light (curve 16). If the same material is irradiated through the grey filter 4, only 50% (curve 18) of the emission excited without damping will be obtained as a result of the higher damping of the 300-nm line.

Because of the wide-band damping behavior of the filter 3, the level of the curve 21 (FIG. 5) hardly differs from that of the curve 18. As a result of the partial damping 19 of the main excitation band of the "genuine" material, however, the emission spectrum 22 generated with the special filter 3 reaches only 20% of the possible final value 16 ($I_e$).

To avoid any undefined lighting conditions on the sample 2 and on the photodetector 11, the whole arrangement described with the aid of FIG. 1 is housed in a light-tight case where the sample can be examined without being reached by ambient light. To ensure that only the ultraviolet light coming from the exciting source 1 reaches the sample to be examined, and that only the radiation emitted by the sample reaches the photodetector 11, the two blocking-filter sets 8, 9 are arranged so that the exciting radiation of the exciting source 1 can reach the sample through the blocking-filter set 8 only, while the radiation emitted by the sample 12 can reach the photodetector 11 only after passing through the blocking-filter set 8. The blocking-filter set 8 is designed so that only the ultraviolet spectrum of the exciting source 1 can pass therethrough without appreciable damping. By contrast, the blocking-filter set 9 blocks this spectral range used for excitation and passes only the radiation emitted by the sample.

Since such blocking-filter sets composed of a large number of different optical filters are commercially available and generally known, their structure will not be described here. Also, since a light-tight case meeting the above requirements can be constructed by a person of ordinary skill in the art without difficulty, it is not shown in the drawings.

Figure 6:
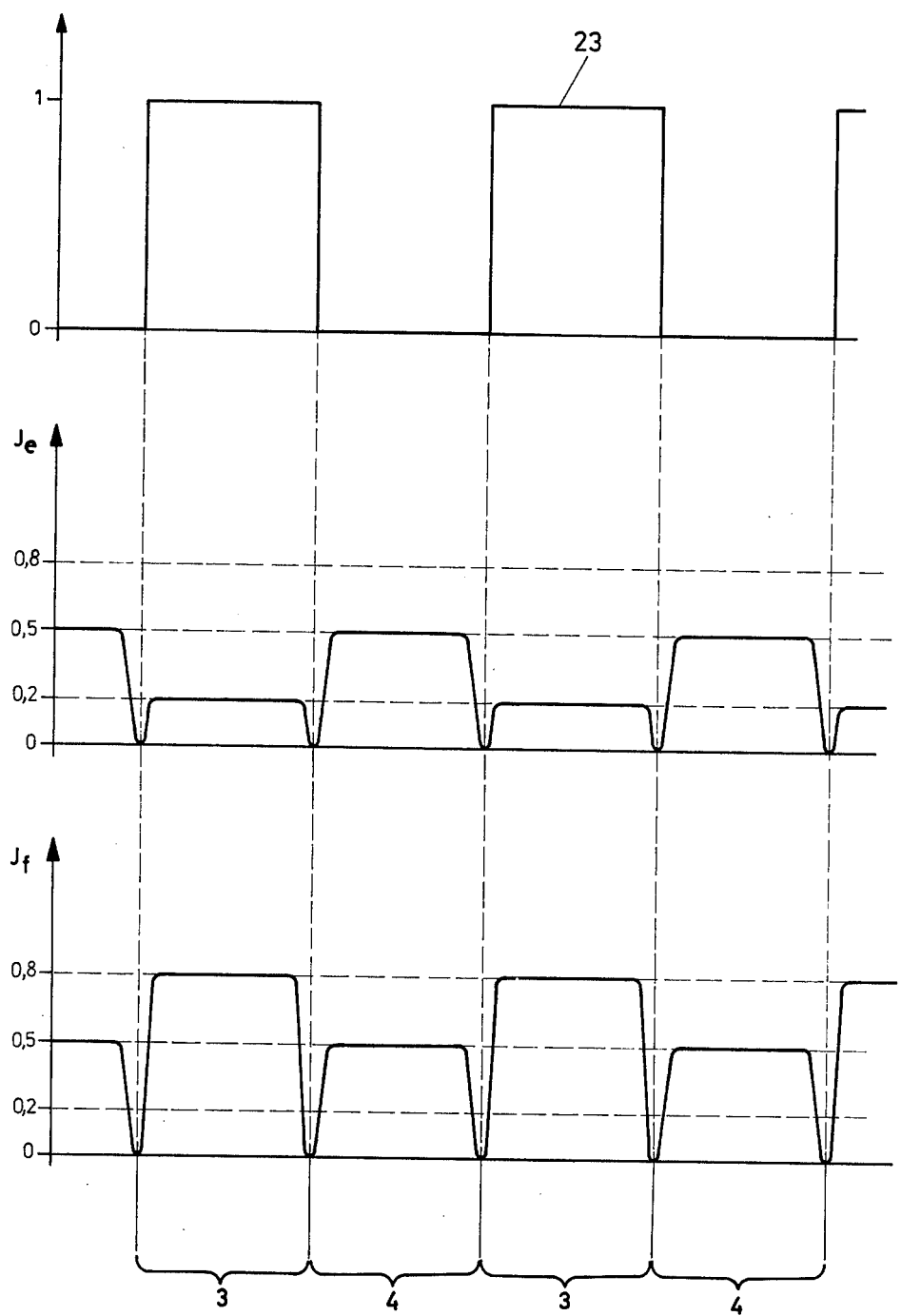
FIG. 6 is a graphic illustration of photodetector signals available in the checking apparatus for evaluation in the case of genuine or selected and false or non-selected fluorescences being checked.

FIG. 6 shows the signals of the position indicator 6 and of the photodetector 11 which are obtained when a "genuine" and a "false" fluorescence signal is being checked. Since the position indicator 6 indicates only the presence and absence of the marking portions 5 of the filter disc, and since a marking portion is just as long as a gap, the position indicator 6 provides a rectangular signal 23 of constant amplitude and fixed mark-to-space ratio. When a genuine fluorescent material is being checked, the photodetector 11 additionally provides similar rectangular signals synchronous with the timing signals of the position indicator 5, but, depending on which filter is located in the exciting-beam path, the amplitudes vary in the rhythm of the timing signals about the levels explained with the aid of FIGS. 4 and 5. When the "genuine" material is irradiated, about 20 or about 50%, of the maximum photocurrent attainable with undamped excitation, are alternately obtained, depending on whether the europium chelate filter 3 or the grey filter 4 is in the exciting-beam path, while these values alternate between 80 and 50% of the maximum value when a "false" fluorescent material is being checked.

Figure 7:
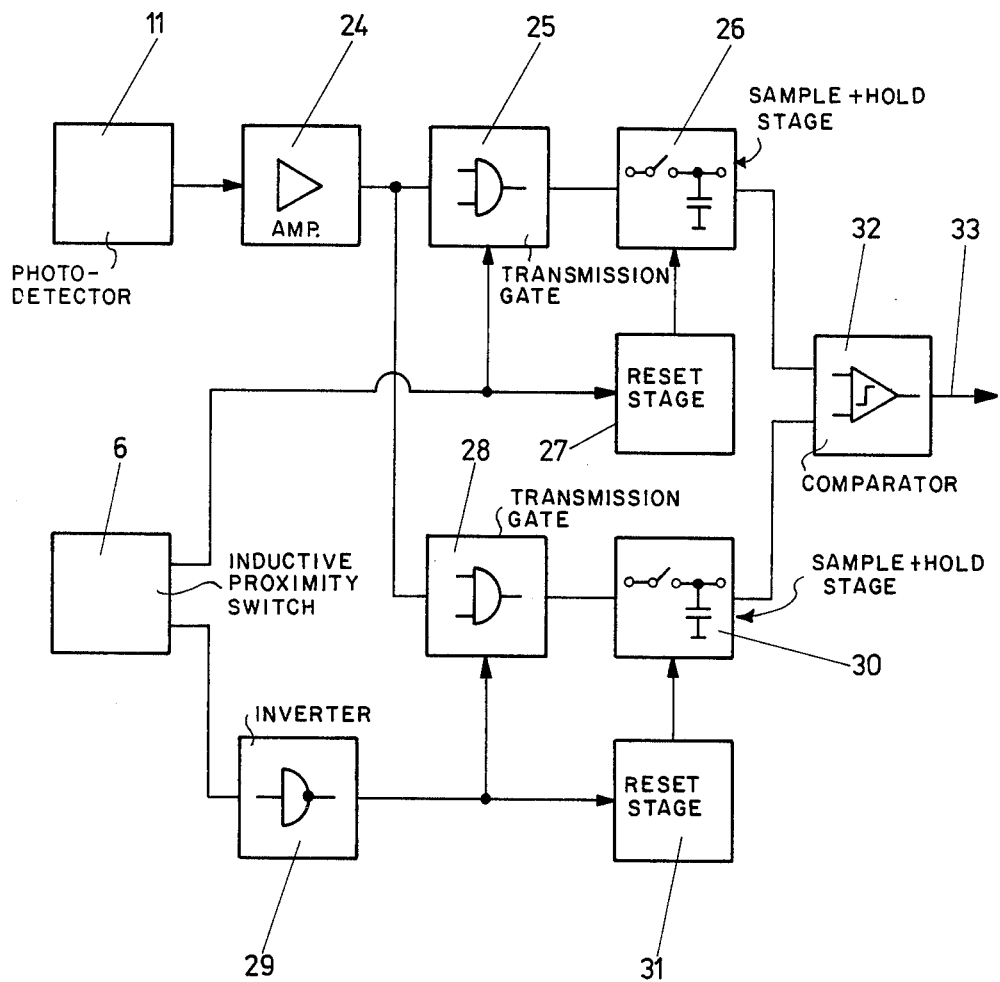
FIG. 7 is a block diagram of an electronic evaluating circuit operable to process the photodetector signals.

FIG. 7 shows, in a block diagram, how the signals of the photodetector 11 and of the position indicator 6 can be processed so that the output of the circuit will provide a logic "high" signal in case of "genuine" fluorescence, and a logic "low" signal in case of "false" fluorescence. With the aid of the position indicator 6, a transmission gate 25 is opened when the europium-chelate filter is located in the beam path, and closed when the grey filter is located in the beam path. An inserted inverter 29 causes the transmission gate 28 to operate in exactly the inverted sense. Thus, if the luminescent material is excited through the europium-chelate filter 3, the sample-and-hold stage 26 will integrate and store the photodetector signals amplified in the amplifier 24, while in case of excitation through the grey filter, the sample-and-hold stage 30 will process the fluorescence signals.

Depending on which of the signals is higher after a predetermined time, a following comparator 32 passes a logic "low" or a logic "high" signal to the output 33 of the circuit. To be ready to receive new signals, the sample-and-hold stages 26 and 30 are reset after each checking cycle with the aid of resetting circuits 27 and 31 triggered by the position indicator 6.

Although the method was explained with reference to the europium-chelate fluorescent material, it is not, of course, limited to the checking of this material. Nearly all fluorescent materials whose excitation spectra are suited for identifying the material can be used to make suitable special filters which can be used as in the example described. To make the filters, organic fluorescent materials are in most cases embedded in transparent plastics, while anorganic materials are frequently embedded in glasses. If no such solution can be found, the luminescent material may also be applied to a suitable transparent base with a bonding agent. With a filter so made, however, light losses are likely to occur due to scattering.

Without departing from the principle according to the invention, the light division between the reference beam (with the grey filter 4) and the checking beam (with the special absorption filter 3) need not necessarily be performed with a rotating disc 2. As in all two-beam methods, instead of the principle described here, i.e. alternate measurement of the fluorescence at the same point, the principle of simultaneous measurement at different points may be employed. To do this, the exciting light is passed partly through the grey filter and partly through the special absorption filter disposed beside the grey filter, for example. The two areas of the document to be checked which are differently illuminated in this way are observed with two suitably arranged fluorescence detectors whose signals are compared.

The last described arrangement can also be converted to an arrangement in which the sample area to be examined is so moved on the first-mentioned principle as to be once in front of the special absorption filter and once in front of the grey filter.

Futhermore, the grey filter described in the embodiment may be replaced by a neutral filter. In that case, however, the measured values obtained with the special filter must not be related to a 50% level (curves 18, 21), but to a value of 100% (curve 16).

In the simplest case, the neutral filter can be replaced by a free opening for the passage of the excitation light beam. Also, the special filter 3 can consist of a clear fluid, such as a cuvette, into which the fluorescent material to be identified, or the chemical contents thereof, has been or can be introduced.

While a specific embodiment of the invention has been shown and described in detail to illustrate the application of the principles of the invention, it will be understood that the invention may be embodied otherwise without departing from such principles.

We claim:

1. In a method of identifying fluorescent materials which are excited into fluorescence with light of respectively differently damped spectral radiant intensities, and in which a wide-band-radiating light source whose spectrum is selectively damped over a wide band and partially is used to irradiate the fluorescent materials, the different radiant intensities emitted by the fluorescent materials are compared, and such comparison is used for identification of a selected fluorescent material; the improvement comprising the steps of providing a neutral filter uniformly damping the radiation of said light source; providing a respective partially absorbing filter damping only the wavelengths necessary to excite the fluorescence of a selected fluorescent material; interposing said filters in the path of light rays directed from said light source onto a sample to be checked for the presence of a selected fluorescent material; measuring the respective intensities of radiation of the sample effected by said neutral filter and by each partially absorbent filter; and converting the measured intensities of radiation into output signals indicative of the presence or absence of the selected fluorescent material.

2. A method as claimed in claim 1, including the steps of using, as the neutral filter, a wide-band-absorbing grey filter.

3. A method as claimed in claim 1, including the steps of moving the neutral filter and each partially absorbing filter alternately into the path of light rays directed from the light source onto the sample.

4. A method as claimed in claim 1, in which the identifying of the fluorescent materials is effected by a two-beam method by directing one beam through said neutral filter and the other beam through a respective partially absorbing filter.

5. A method as claimed in claim 4, in which the light rays from said light source are directed alternately through the neutral filter and a respective partially absorbing filter in succession.

6. A method as claimed in claim 4, in which the beams are directed simultaneously through the neutral filter and the respective partially absorbing filter.

7. A method as claimed in claim 4, including using, as the neutral filter, a free opening for the passage of light rays directed from said light source onto the sample.

8. A method as claimed in claim 1, including the steps of providing a plurality of partially absorbing filters each respective to a selected fluorescent material; and directing light rays from said light source through said neutral filter and said partially absorbing filters to distinguish between plural fluorescent materials.

9. A method as claimed in claim 8, in which the light rays from said light source are directed alternately through said neutral filter and successive ones of said partially absorbing filters.

10. A method as claimed in claim 8, in which the light rays from said source are directed simultaneously through said neutral filter and through said partially absorbing filters.

11. A method as claimed in claim 1, in which each partially absorbing light filter is designed as an optical absorption filter containing an addition of the selected fluorescent material to be identified.

12. A method as claimed in claim 11, in which such addition comprises at least one of the chemical components of the selected fluorescent material to be identified.

13. A method as claimed in claim 11, in which the addition is applied to a transparent base by means of a bonding agent.

14. A method as claimed in claim 11, in which the addition is applied to a filter surface through the medium of a solution.

15. A method as claimed in claim 11, in which each partially absorbing filter consists of a clear, solid fluid containing such addition.

16. A method as claimed in claim 15, in which the clear, solid fluid is glass.

17. A method as claimed in claim 11, in which each partially absorbing filter consists of a clear fluid into which the addition is introduced.

* * * * *